(12) United States Patent
Burke

(10) Patent No.: US 10,583,243 B2
(45) Date of Patent: Mar. 10, 2020

(54) INTRAVENOUS LINE ORGANIZING SYSTEM

(71) Applicant: Derryl Burke, Montréal (CA)

(72) Inventor: Derryl Burke, Montréal (CA)

(*) Notice: Subject to any disclaimer, the term of this patent is extended or adjusted under 35 U.S.C. 154(b) by 28 days.

(21) Appl. No.: 14/894,830

(22) PCT Filed: Apr. 2, 2014

(86) PCT No.: PCT/CA2014/050330
§ 371 (c)(1),
(2) Date: Nov. 30, 2015

(87) PCT Pub. No.: WO2014/190424
PCT Pub. Date: Dec. 4, 2014

(65) Prior Publication Data
US 2016/0114103 A1    Apr. 28, 2016

Related U.S. Application Data

(60) Provisional application No. 61/829,526, filed on May 31, 2013.

(51) Int. Cl.
*A61M 5/14* (2006.01)
*A61M 25/02* (2006.01)

(52) U.S. Cl.
CPC ........ *A61M 5/1418* (2013.01); *A61M 5/1415* (2013.01); *A61M 25/02* (2013.01);
(Continued)

(58) Field of Classification Search
CPC .. A61M 5/1418; A61M 5/1415; A61M 25/02; A61M 2005/1416;
(Continued)

(56) References Cited

U.S. PATENT DOCUMENTS 2,880,949 A * 4/1959 Fuss ................. F16L 3/227
248/70
3,696,920 A  10/1972 Lahay
(Continued)

FOREIGN PATENT DOCUMENTS

NL    8302022      1/1985
WO    03/082396   10/2003

OTHER PUBLICATIONS

International Search Report (ISR) (PCT Form PCT/ISA/210) dated Jul. 7, 2014, in PCT/CA2014/050330.
(Continued)

*Primary Examiner* — Brandy S Lee
*Assistant Examiner* — Hong-Van N Trinh
(74) *Attorney, Agent, or Firm* — BakerHostetler

(57) ABSTRACT

An intravenous line organizing system to be attached to patients to organize one or several IV lines, preventing entanglement and contamination by dragging on the floor, while allowing patient mobility. The hypoallergenic device can be strapped with a band around a patient's limb or torso, or adhered to the skin anywhere on the body. Each clip element allows one IV line to float freely through it. Each clip element rotates 360° and can move horizontally within a channel in the system, or it can be pushed into a locked position, preventing rotation and horizontal movement.

6 Claims, 12 Drawing Sheets

(52) U.S. Cl.
CPC .............. *A61M 2005/1416* (2013.01); *A61M 2025/024* (2013.01); *A61M 2025/026* (2013.01); *A61M 2025/0206* (2013.01); *A61M 2025/028* (2013.01); *A61M 2025/0213* (2013.01); *A61M 2025/0253* (2013.01)

(58) Field of Classification Search
CPC .. A61M 2025/0206; A61M 2025/0213; A61M 2025/024; A61M 2025/0253; A61M 2025/026; A61M 2025/028; Y10S 128/06; Y10S 128/026; Y10T 24/344; Y10T 24/3444
USPC .................................................. 220/324, 326
See application file for complete search history.

(56) References Cited

U.S. PATENT DOCUMENTS

| | | | |
|---|---|---|---|
| 3,747,166 A | 7/1973 | Eross | |
| 3,782,388 A | 1/1974 | Page | |
| 4,025,015 A * | 5/1977 | Kolic | F16L 3/08 128/DIG. 26 |
| 4,707,906 A | 11/1987 | Posey | |
| 4,906,234 A | 3/1990 | Voychehovski | |
| 5,100,393 A * | 3/1992 | Johnson | A61M 25/02 128/DIG. 26 |
| 5,195,981 A * | 3/1993 | Johnson | A61M 25/02 128/DIG. 26 |
| 5,224,674 A * | 7/1993 | Simons | F16L 3/2235 248/68.1 |
| 5,336,179 A | 8/1994 | Ryan | |
| 5,345,931 A * | 9/1994 | Battaglia, Jr. | A61M 16/0488 128/207.17 |
| 5,437,273 A * | 8/1995 | Bates | A61M 16/0488 128/207.14 |
| 5,490,504 A * | 2/1996 | Vrona | A61M 16/0488 128/207.14 |
| 5,507,460 A * | 4/1996 | Schneider | A61M 5/1418 24/601.2 |
| 5,690,617 A | 11/1997 | Wright | |
| 5,944,696 A | 8/1999 | Bayless et al. | |
| 6,067,985 A * | 5/2000 | Islava | A61M 16/0488 128/207.17 |
| 6,228,064 B1 | 5/2001 | Abita et al. | |
| 6,458,104 B2 | 10/2002 | Gautsche | |
| 6,578,576 B1 * | 6/2003 | Taormina | A61M 16/0488 128/200.24 |
| 7,090,174 B2 * | 8/2006 | Korczak | F16L 3/222 248/61 |
| 7,456,361 B2 * | 11/2008 | Hill | H01R 4/48 174/84 C |
| 8,302,597 B2 * | 11/2012 | Beely | A61M 16/0493 128/200.26 |
| 2001/0049504 A1 * | 12/2001 | Gautsche | A61M 5/1418 604/174 |
| 2005/0234405 A1 | 10/2005 | Dikeman et al. | |
| 2008/0294117 A1 * | 11/2008 | Ware | A61M 5/1418 604/174 |
| 2011/0126839 A1 * | 6/2011 | Levine | A61M 16/0497 128/207.14 |
| 2011/0210215 A1 * | 9/2011 | Nitsche | F16L 3/24 248/74.1 |
| 2011/0240034 A1 * | 10/2011 | Ciccone | A61M 16/0493 128/207.17 |
| 2012/0152944 A1 * | 6/2012 | Vilkomirski | B25H 3/022 220/4.28 |
| 2012/0168571 A1 * | 7/2012 | Bond | A61M 25/02 248/70 |
| 2012/0227747 A1 * | 9/2012 | Levine | A61M 16/0497 128/207.14 |
| 2014/0261462 A1 * | 9/2014 | Visconti | A61M 16/0497 128/861 |
| 2014/0261463 A1 * | 9/2014 | Visconti | A61M 16/0493 128/861 |
| 2014/0358090 A1 * | 12/2014 | Wainscott | A61M 25/02 604/179 |
| 2016/0271349 A1 * | 9/2016 | Zickefoose | A61M 16/0497 |
| 2017/0197049 A1 * | 7/2017 | Doll | A61M 16/0488 |

OTHER PUBLICATIONS

European Search Report for Application No. 14805140.2, dated Jan. 23, 2017, 8 pages.

* cited by examiner

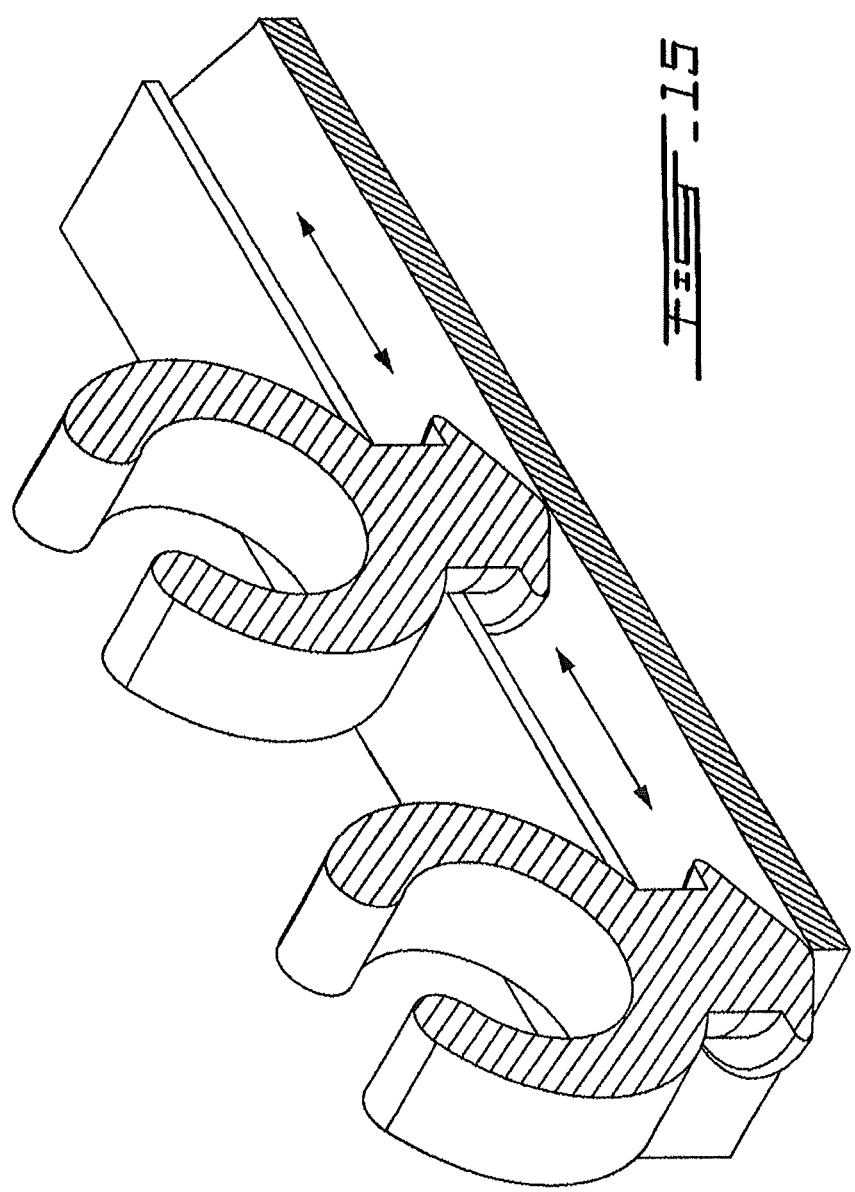

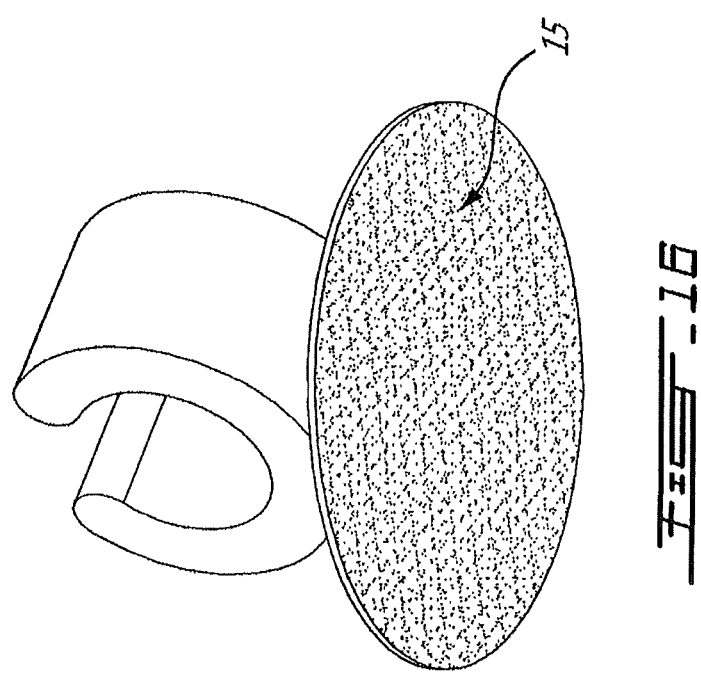

INTRAVENOUS LINE ORGANIZING SYSTEM

REFERENCE TO RELATED APPLICATIONS

This application is the U.S. national stage of International Application No. PCT/CA2014/050330, filed Apr. 2, 2014, which claims the priority of U.S. Provisional Application No. 61/829,526, filed May 31, 2013, the disclosures of which are all incorporated herein by reference in their entireties.

FIELD OF THE INVENTION

The present invention generally relates to intravenous line separator systems. More particularly, this invention relates to a plastic channel device which retains single or multiple rotating clip holders for intravenous or catheter tubes and is attached to a cuff for securement on a human limb.

BACKGROUND OF THE INVENTION

Hospital patients are often encumbered with individual intravenous or catheter tubes which become entangled with the patients' clothing, bedding, and/or each other, restricting the patients' movement.

In observation, post-op patients and patients receiving oncology treatments, there are multiple IV lines going into the patients. Lines often get tangled in each other. When receiving chemotherapy, the lines are taped onto the patients' skin to keep the IV lines stable. When patients are post-op and lying in bed, if the patient is not still and sedentary, lines are often on the right and left hand side of the patient. They get tangled together. When the patient moves from the right to the left, these lines can often get pulled out.

During post op procedures, doctors ask their patients to walk in the hospital hallways for exercise. Patients are still on IVs for their medications and hydration. To enable the patient to exercise, the IVs are on a rolling stand and the lines may drag on the floor and can become contaminated or caught up in the wheels of the rolling stand. When patients using walkers have IV lines, the lines are often left dangling and dragging on the floor, or they can get caught up in the front wheels of the walker.

Typically, very often there is only surgical tape to hold the IV lies in place and when the IV lines are removed with the tape, the tape catches the hair of the patients' body. In other cases, the tape may not always hold. The problem with these approaches is that prior art systems do not adequately address the problem of disorganization, tangling/dragging of IV lines.

Prior art documents known to the Applicant include:

| U.S. Pat. No. | Title | Publication Date |
|---|---|---|
| 5,690,617 | Adjusting catheter holding device | 1997 |
| 6,458,104 | IV administration lines fastening and identification device | 2002 |
| 3,696,920 | Device for organizing objects | 1972 |
| 3,782,388 | Medical tube holder | 1974 |
| 5,944,696 | Swivel clip medical tube holder | 1999 |
| 6,228,064 | Intravenous anchor system | 2001 |
| 2001/0049504 | IV administration lines fastening and identification device | 2001 |
| 2005/0234405 | Site securement device for securing intravascular tubing | 2005 |
| 3,747,166 | Hose holder | 1973 |
| 4,707,906 | Method of attaching tube to a tube holder | 1987 |
| 5,507,460 | Tubing holder especially for patient applications | 1996 |
| 5,336,179 | Line organizer | 1994 |

However, there is still a need for an intravenous line organizing system that addresses at least one of the above-mentioned problems.

SUMMARY OF THE INVENTION

An object of the present invention is to propose a system that satisfies at least one of the above-mentioned needs.

According to the present invention, that object is accomplished with a system attachable to the bodies of medical patients for purposes of organizing single or multiple IV lines to prevent disorganization, tangling, and dragging.

A non-restrictive description of a preferred embodiment of the invention will now be given with reference to the appended drawings.

BRIEF DESCRIPTION OF THE DRAWINGS

FIG. 15 is a cross-sectional view showing two clip elements in floating position, according to a preferred embodiment of the present invention.

FIG. 16 is a perspective view of a singular clip element with an adhesive bottom, according to another preferred embodiment of the present invention.

PREFERRED EMBODIMENTS OF THE PRESENT INVENTION

An object of the present invention is to provide an intravenous line organizing system.

Figure 2:
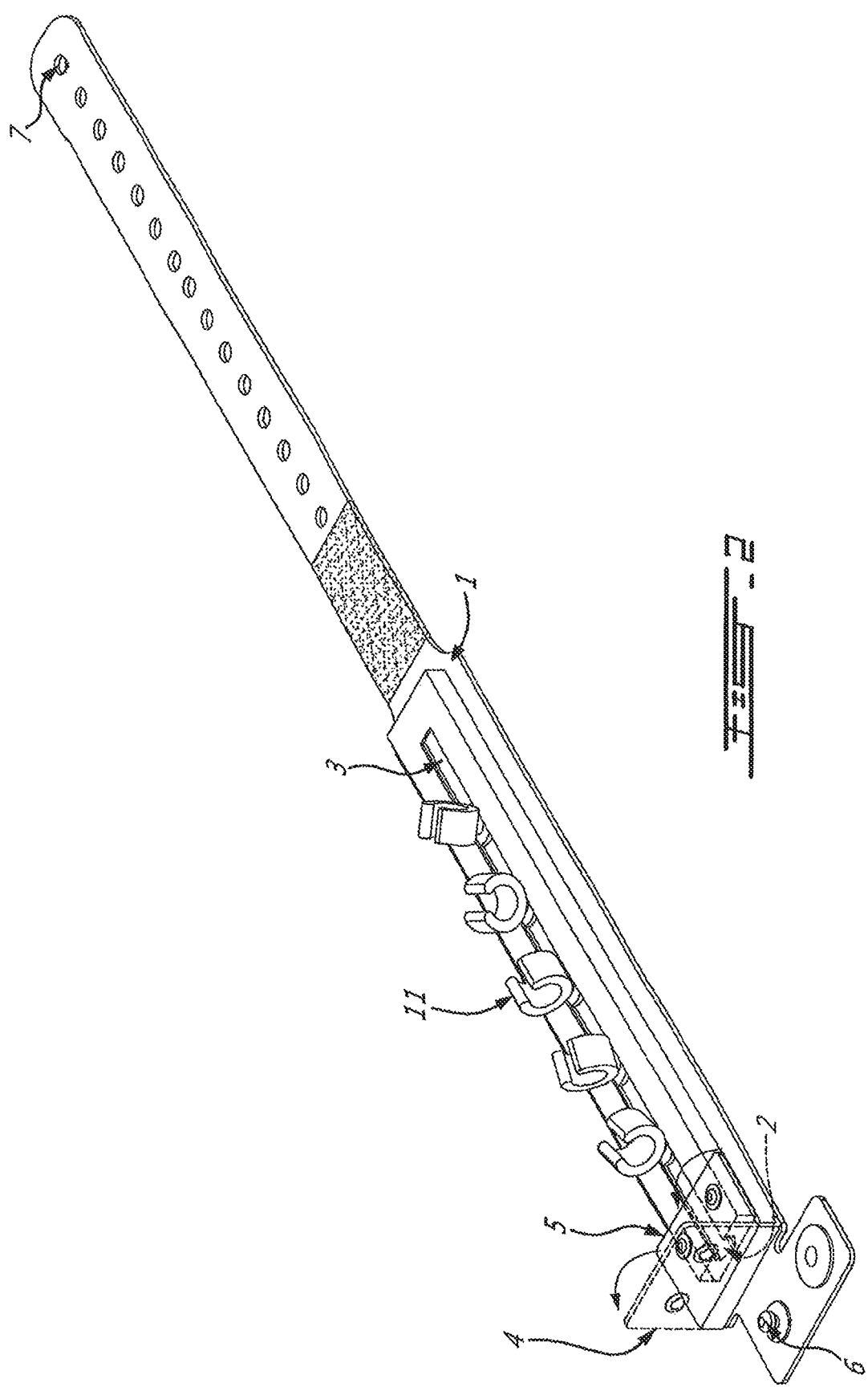
FIG. 2 is a perspective view of the first system shown in FIG. 1 showing the locking mechanisms and five rotating IV line holders.
Figure 3:
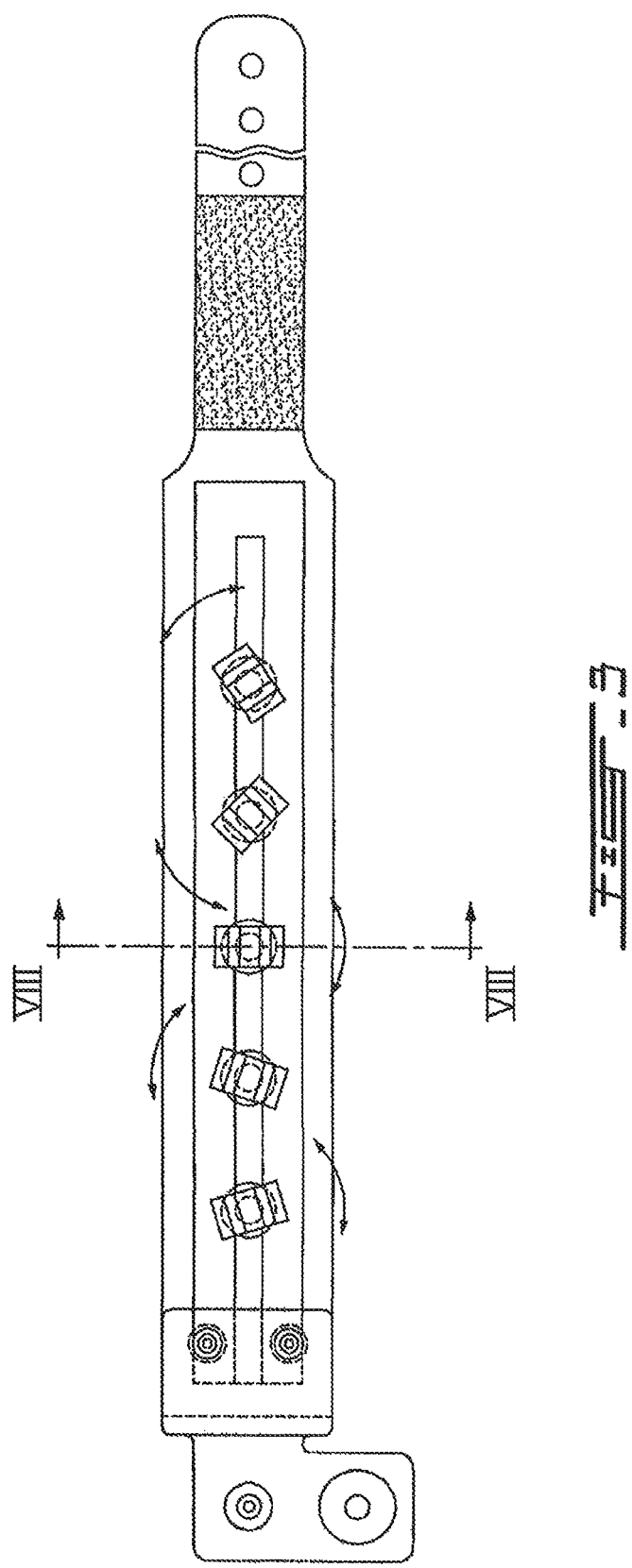
FIG. 3 is a top view of the system shown in FIG. 2, with the closing mechanisms in a closed position.
Figure 4:
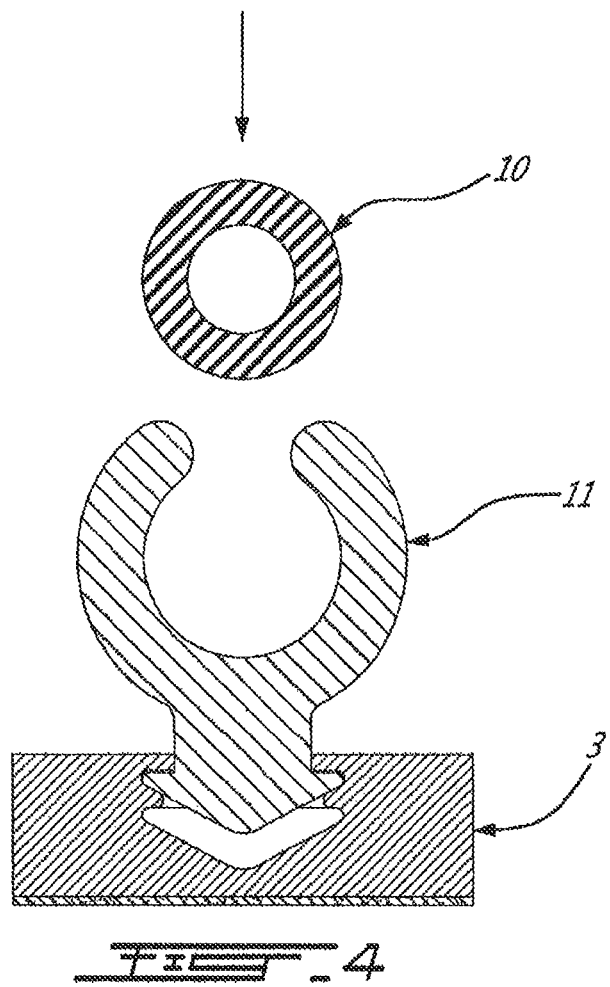
FIGS. 4 and 5 are cross-sectional views showing an intravenous line before and after insertion into a clip element according to a preferred embodiment of the present invention.
Figure 5:
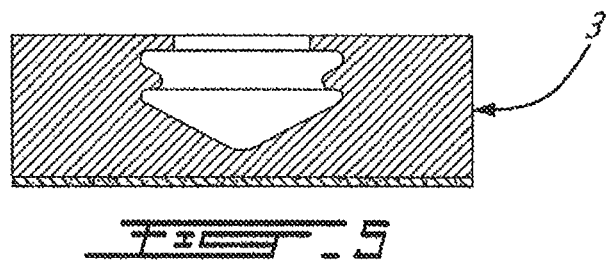
Figure 8:
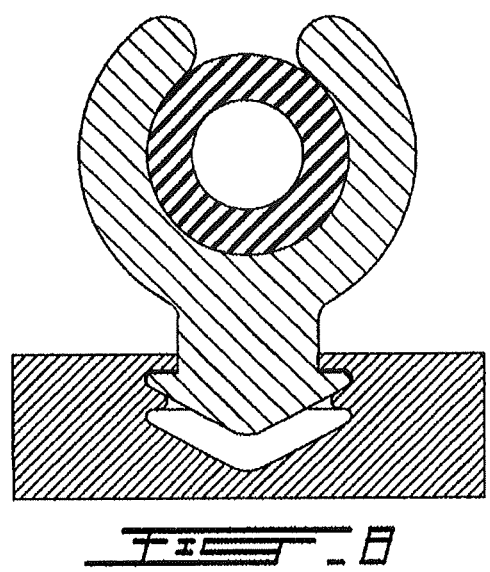
FIGS. 8 and 9 are cross-sectional views showing an IV in a clip element of FIG. 4 in a floating configuration (FIG. 8) and pushed down into a fixed position configuration (FIG. 9), according to a preferred embodiment of the present invention.
Figure 9:
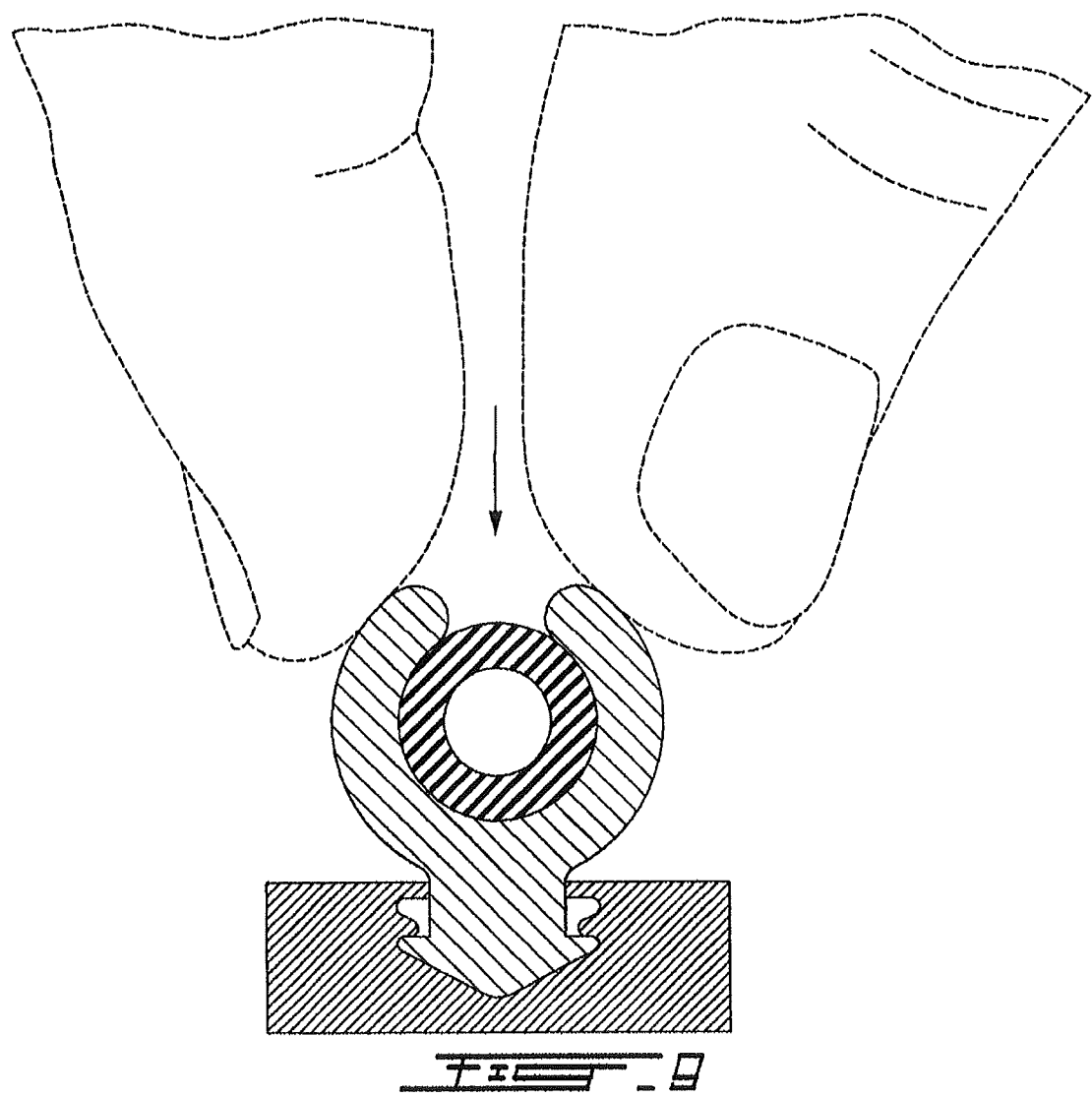
Figure 10:
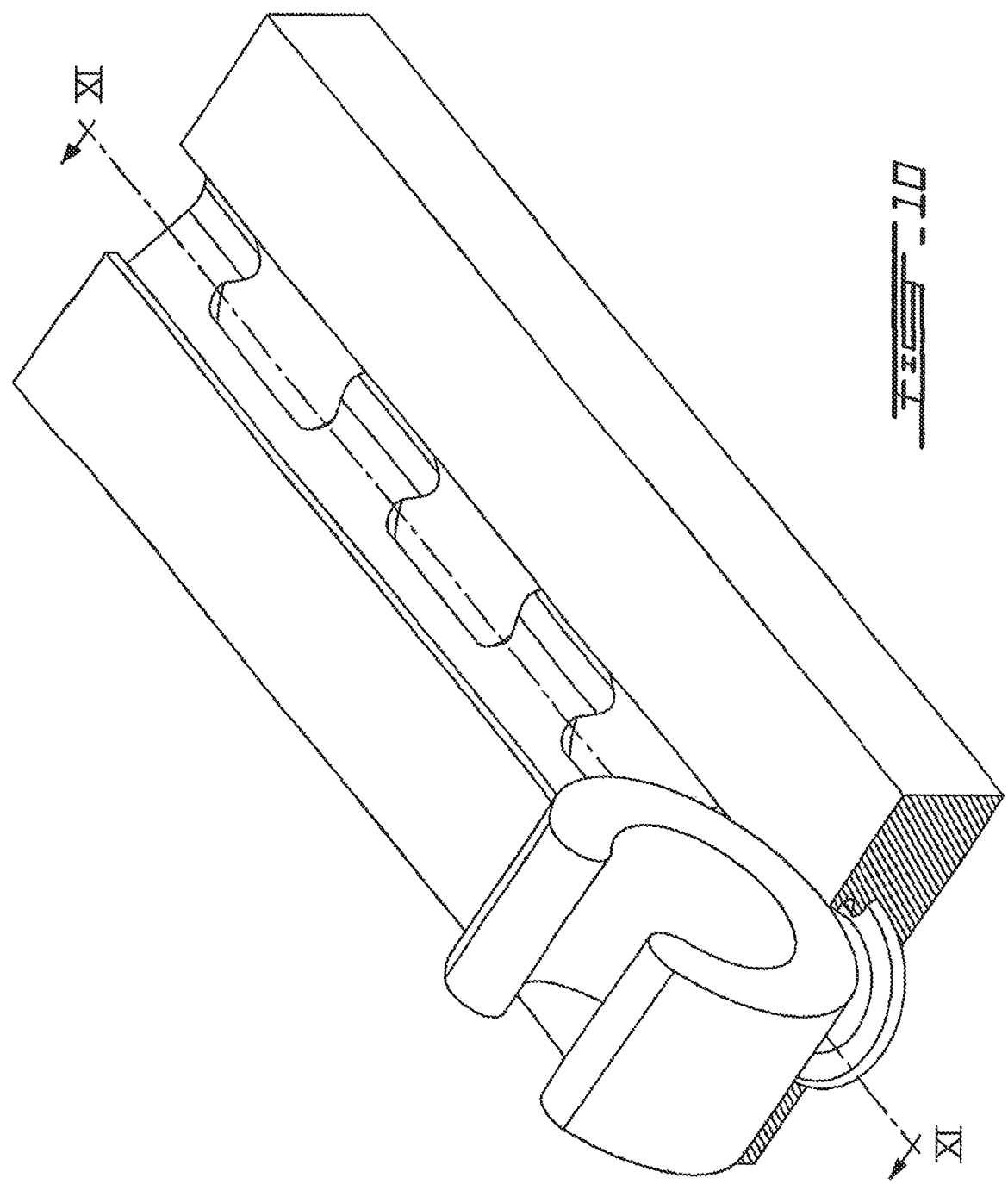
FIG. 10 is a perspective view of one clip element in a fixed position configuration, according to a preferred embodiment of the present invention.
Figure 11:
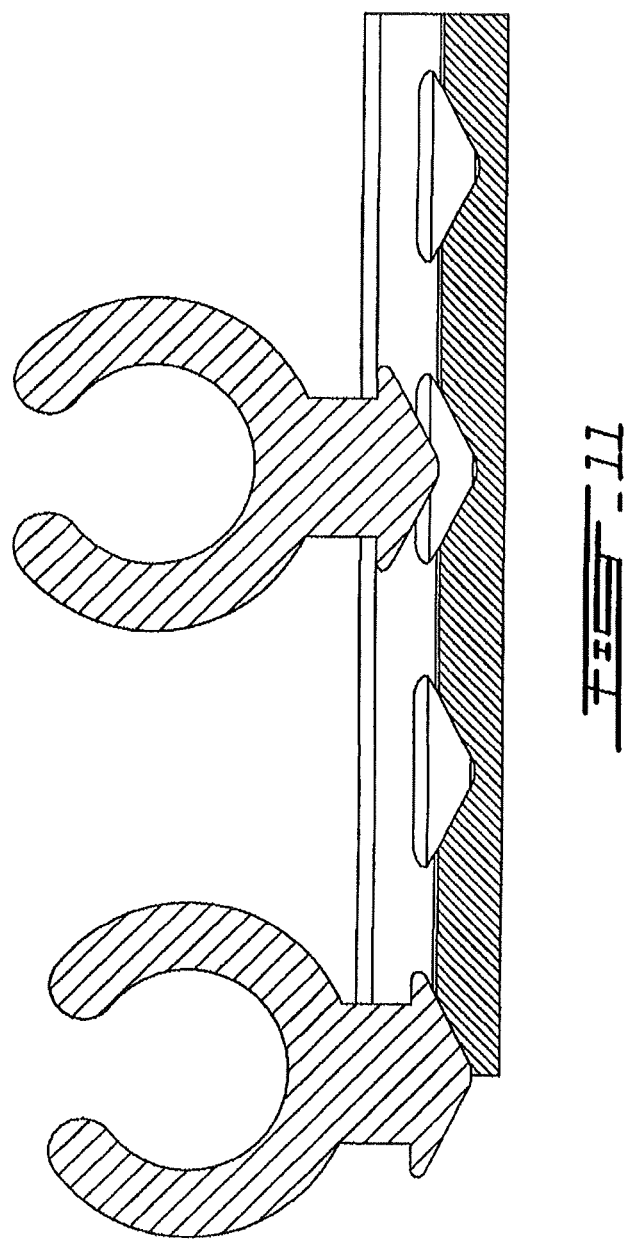
FIG. 11 is a cross-sectional view of two clip elements, one floating in the channel, and one fixed, according to a preferred embodiment of the present invention.
Figure 12:
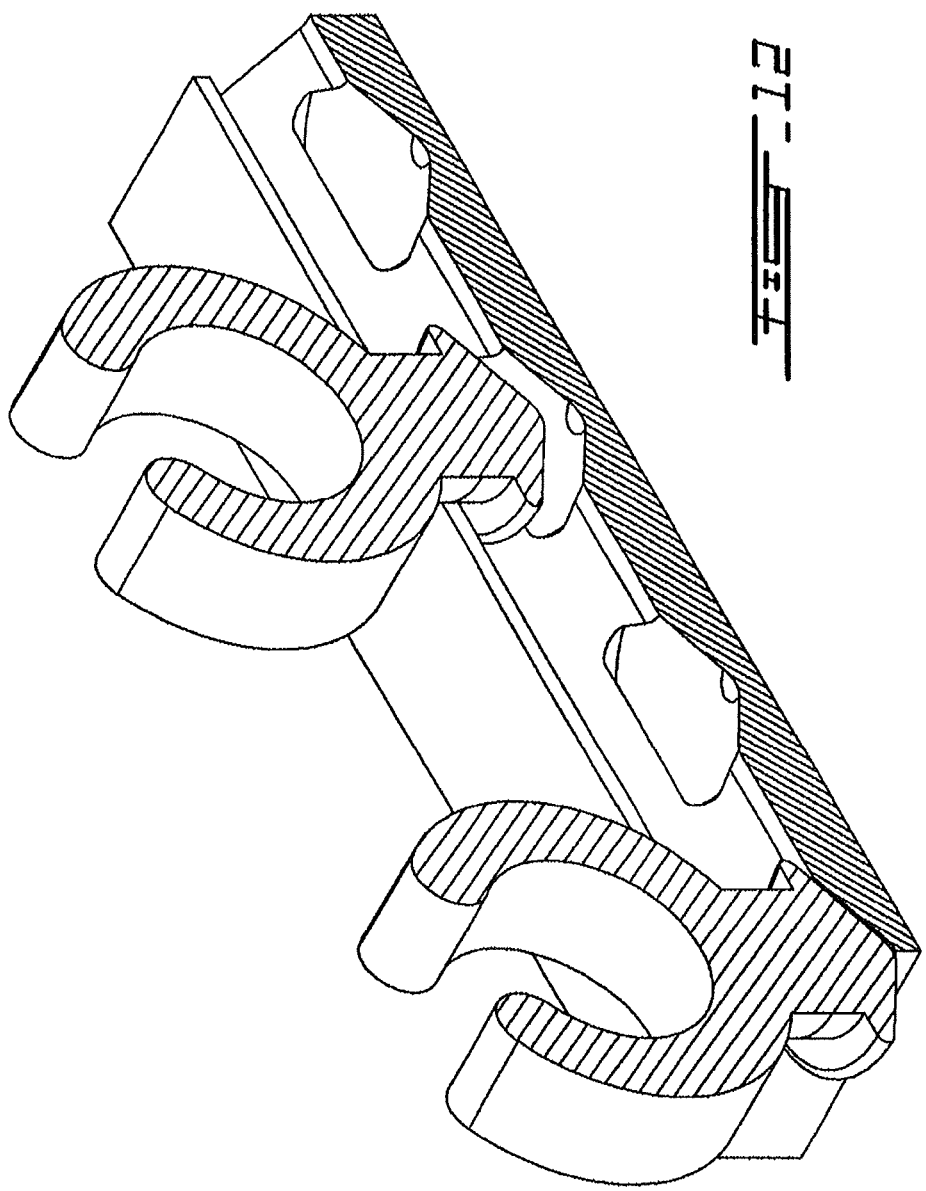
FIG. 12 is a perspective cross-sectional view of FIG. 11.
Figure 14:
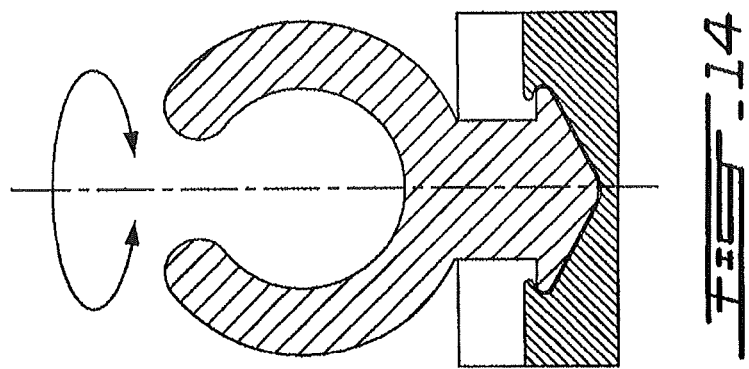
FIG. 14 is a cross-sectional view of a singular clip element in a fixed position, showing its 360° rotation capability, according to a preferred embodiment of the present invention.
Figure 13:
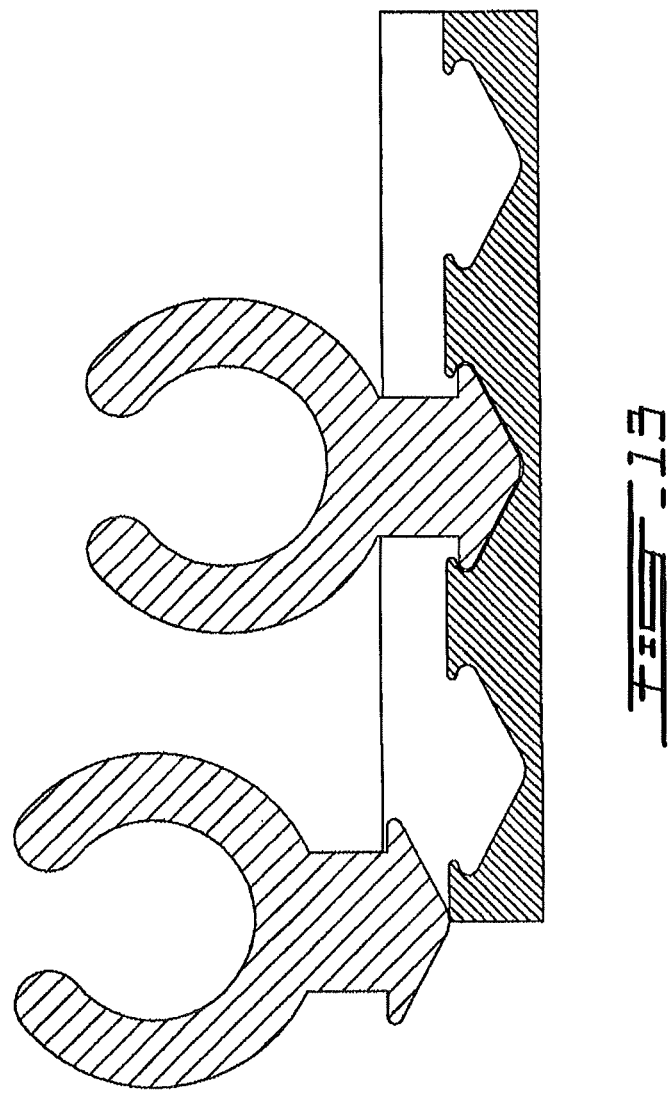
FIG. 13 is a cross-sectional view of two clip elements, one floating in the channel, and one fixed, according to a preferred embodiment of the present invention.

As better shown in FIG. 2, there is provided an intravenous line organizing system comprising patient attachment means 1 for attaching the system to a patient. The system also includes a base channel element 3 attached to the patient attachment means 1. At least one clip element 11 can be secured to the base channel element 3. As better shown in FIGS. 4, 8 and 9, each clip element 11 is shaped to receive a medical tube 10 and each clip element 11 is removably securable to the base channel element 3 between a floating configuration (shown in FIG. 4 or 8) wherein the clip element 11 is rotatable with respect to the channel element 3 and displaceable along a direction of the channel element, and a locked configuration (shown in FIG. 9) wherein the clip element 11 is fixed with respect to the channel element 3.

In one scenario, the patient attachment means 1 is an adjustable band, as shown in FIG. 2.

In another scenario, the patient attachment means is an adhesive pad 15, as shown in FIG. 16.

In another embodiment of the present invention, the system can be provided as a kit including a plurality of clip elements adjustable to different medical tube diameters.

Figure 1:
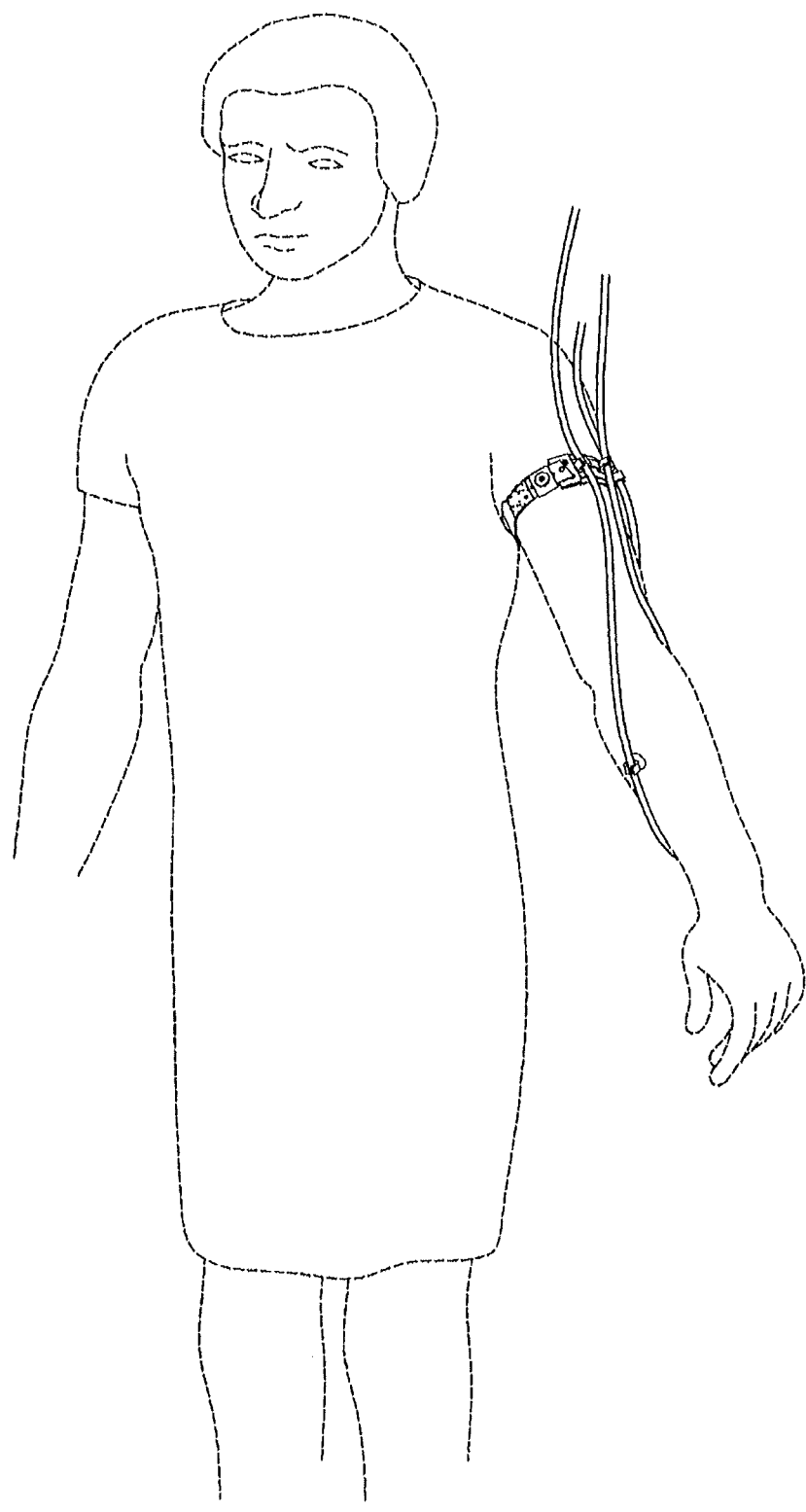
FIG. 1 is a perspective view of two embodiments of the present invention in an assembled state, attached to a patient's arm: a first system organizing multiple IV lines, and a second system holding one single IV line, according to a preferred embodiment of the present invention.

FIG. 1 shows two versions of the present invention in an assembled state, attached to a patient's arm. The band on the upper arm is holding multiple IV lines. A singular clip element with an adhesive backing is attached to the forearm.

FIG. 2 shows an organizing system in assembled state, before being closed around a patient's limb or torso. Clip elements are inserted into the band through a channel opening and can float freely within the channel, or be pushed down into a fixed position. A closing mechanism 4 prevents floating clip elements 11 from exiting the base channel element 3 via an open distal end 2. The lid of the closing mechanisms flips open and closes securely by means of two snaps 5. The band may be wrapped around a patient's limb or torso and secured by placing a protruding nipple 6 through one of the holes 7 in the band, accommodating various sizes.

Preferably, all parts of the system are made from a variety of rigid and pliable polymer plastics, and designed to be comfortable for the patient.

Preferably, a clip element can be set to a particular degree of rotation, depending on angle of the intravenous line, and locked in a fixed position, or it can be allowed to rotate horizontally 360°, to accommodate a patient's movements.

Figure 6:
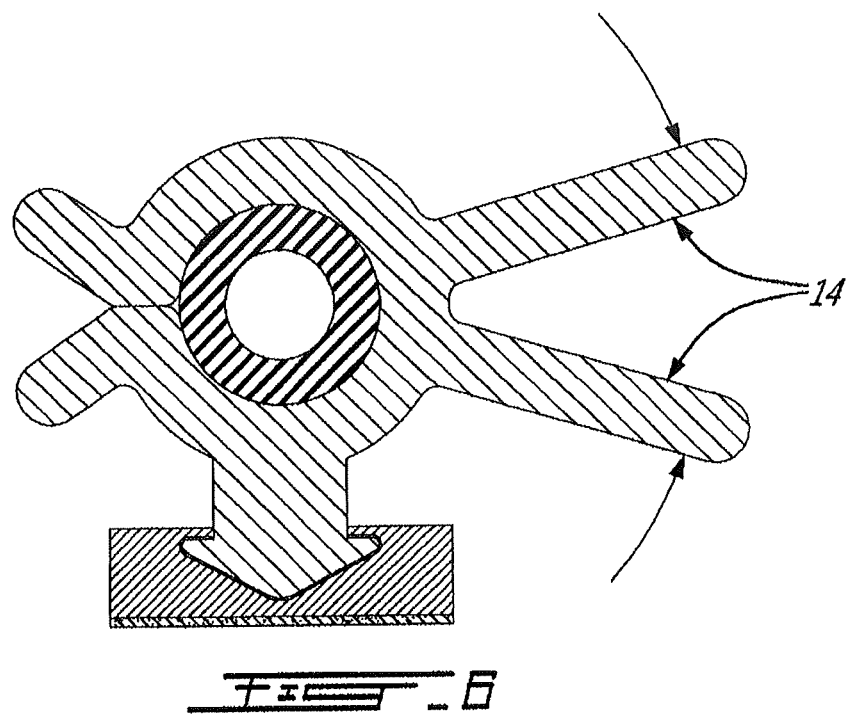
FIGS. 6 and 7 are cross-sectional views of an IV clip element that opens and closes, showing an IV line before and after insertion, according to another preferred embodiment of the present invention.
Figure 7:
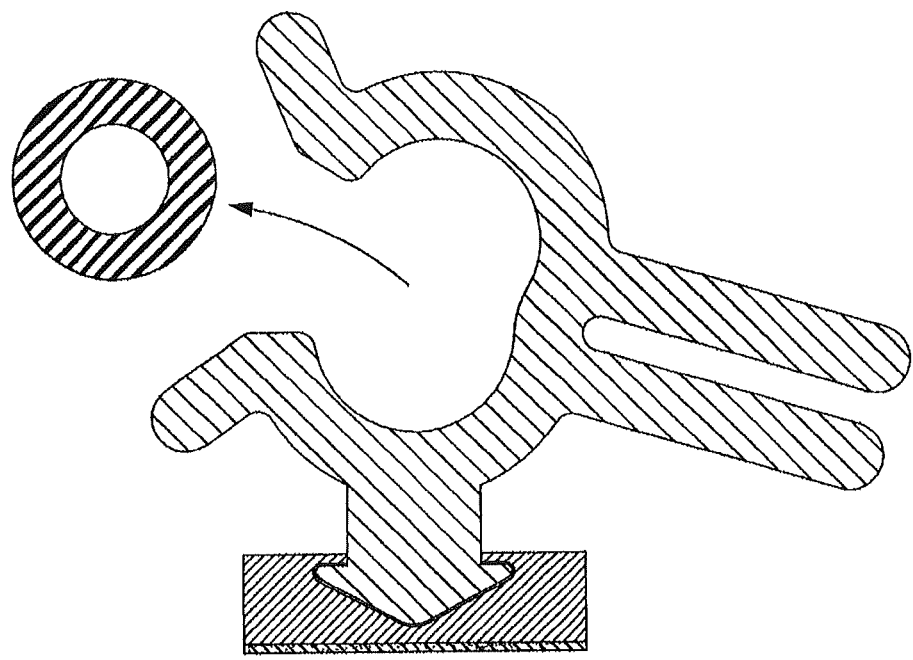

Preferably, whether the clip elements are locked or rotating, intravenous lines can float freely through them. The medical tube of the intravenous line can be inserted in an open loop of the clip element 11. The open loop can include an aperture for insertion of the medical tube 10 as seen on FIG. 4, or the open loop can be splayed opened by squeezing two levers 14 toward on another as seen on FIG. 6.

Preferably, the patent attachment means or band is made in a range of sizes so that it can be wrapped around the torsos and limbs of patients of all sizes.

Preferably, a system can hold one or several clip elements, and individual clips can be removed or added easily.

Preferably, the risk of contamination to IV lines is reduced by preventing the lines from coming into contact with floors.

Preferably, the adhesive backing of the singular clip element is hypoallergenic.

Preferably, in certain scenarios, one or several singular clip elements can be adhered to a patient.

Although preferred embodiments of the present invention have been described in detail herein and illustrated in the accompanying drawings, it is to be understood that the invention is not limited to these precise embodiments and that various changes and modifications may be effected therein without departing from the scope of the present invention.

The invention claimed is:

1. An intravenous line organizing system comprising:
a base structure attachable to a patient;
a base channel element mounted about the base structure, the base channel element comprising:
an elongated channel being recessed with respect to a top surface of the base channel element, and
plurality of secondary cavities being further recessed with respect to the elongated channel and being in communication with the elongated channel; and
at least one clip element having a distal end being shaped to receive an intravenous line, and a proximal end being inserted into the base channel element so as to selectively assume:
a floating configuration in which the proximal end of the at least one clip element is slidably retained within the elongated channel for displacement of the at least one clip element along a direction of the elongated channel and above the plurality of secondary cavities in response to movements of the patient, and
a locked configuration in which the proximal end of the at least one clip element is engaged within one of the plurality of secondary cavities by pushing the at least one clip element from the elongated channel into the one of the plurality of secondary cavities perpendicularly to the direction of the elongated channel, the at least one clip element being fixed with respect to the base channel element.

2. The intravenous line organizing system according to claim 1, wherein the base structure is an adjustable band.

3. The intravenous line organizing system according to claim 1, wherein the base structure is an adhesive pad.

4. The intravenous line organizing system according to claim 1, wherein the at least one clip element comprises a plurality of clip elements adjustable to different intravenous line diameters.

5. The intravenous line organizing system according to claim 1, wherein the base channel element has a distal end which is open to create a passage for the at least one clip element to enter or exit the elongated channel, the intravenous line organizing system further comprising a lid removably closing the open distal end.

6. The intravenous line organizing system according to claim 1, wherein each of the at least one clip element comprises an open loop element to slidably engage the intravenous line.

* * * * *